United States Patent [19]

Leighton et al.

[11] Patent Number: 5,415,926

[45] Date of Patent: May 16, 1995

[54] PROCESS FOR REDUCING THE FREE ALDEHYDE CONTENT IN N-ALKYLOL AMIDE MONOMERS

[75] Inventors: John C. Leighton, Flanders; Rama S. Chandran, South Bound Brook, both of N.J.

[73] Assignee: National Starch and Chemical Investment Holding Coporation, Wilmington, Del.

[21] Appl. No.: 23,268

[22] Filed: Feb. 25, 1993

[51] Int. Cl.⁶ ............................................. D04H 1/64
[52] U.S. Cl. .................. 428/288; 526/303.1; 526/304; 528/230; 548/547; 560/160; 562/567; 564/208; 427/392; 428/290; 428/361
[58] Field of Search .................. 548/547; 560/160; 562/567; 564/208; 526/303.1, 304; 528/230; 428/288, 290, 360, 361

[56] References Cited

U.S. PATENT DOCUMENTS

| | | |
|---|---|---|
| 3,380,851 | 4/1968 | Lindemann et al. |
| 3,422,139 | 1/1969 | Talet et al. ............................ 260/534 |
| 3,678,133 | 7/1972 | Ryan ................................... 260/876 R |
| 3,708,388 | 1/1973 | Lindemann et al ................. 161/247 |
| 3,714,099 | 1/1973 | Biale ............................ 260/29.67 TA |
| 4,086,296 | 4/1978 | Carty et al. ...................... 260/857 G |
| 4,094,849 | 6/1978 | Oyamada et al. ........... 260/29.6 MQ |
| 4,164,488 | 8/1979 | Gregorovich et al. ............. 260/29.4 |
| 4,189,370 | 2/1980 | Boschetti ........................ 204/299 R |
| 4,267,277 | 5/1981 | Korf ..................................... 521/103 |
| 4,289,676 | 9/1981 | Czauderna et al. ........... 260/29.6 H |
| 4,360,632 | 11/1982 | Pinschmidt, Jr. et al. ......... 524/819 |
| 4,439,574 | 3/1984 | Schuppiser et al. ................ 524/458 |
| 4,449,978 | 5/1984 | Iacoviello ........................... 604/372 |
| 4,481,250 | 11/1984 | Cook et al. ........................... 428/290 |
| 4,590,102 | 5/1986 | Rosamilia et al. ................ 427/374.1 |
| 4,647,611 | 3/1987 | Goldstein et al. .................... 524/458 |
| 4,663,410 | 5/1987 | Pinschmidt, Jr. et al. .......... 526/263 |
| 4,745,025 | 5/1988 | Mao ..................................... 428/288 |
| 4,814,226 | 3/1989 | Goldstein ............................. 428/288 |
| 4,814,373 | 3/1989 | Frankel et al. ....................... 524/460 |
| 4,959,249 | 9/1990 | Schilling et al. ..................... 427/387 |
| 5,079,067 | 1/1992 | Willging .............................. 428/182 |
| 5,137,963 | 8/1992 | Stack .................................... 524/519 |
| 5,143,954 | 9/1992 | Hutton et al. ....................... 524/106 |
| 5,177,263 | 1/1993 | Leighton et al. .................... 564/186 |

FOREIGN PATENT DOCUMENTS 2034217  1/1991  Canada.
1177199  9/1968  United Kingdom.

OTHER PUBLICATIONS

American Cyanamid Company, Wayne, New Jersey; PRC-485; "NMA Special".
Morton International, Inc., "Pure ® VenPure ®", Process Stream Purification, Technical Manual and Users Guide.

*Primary Examiner*—James C. Cannon
*Attorney, Agent, or Firm*—Ellen T. Dec

[57] ABSTRACT

In a process for the preparation of N-alkylol amide monomers wherein a polymerizable amide is reacted with an aldehyde, the improvement which comprises adjusting the pH of the resulting N-alkylol amide monomer to pH 10–11 and adding thereto an alkali or alkali earth metal borohydride at a temperature of −10° to 20° C. so as to convert the residual free aldehyde in the equilibrium mixture to the corresponding alcohol.

17 Claims, No Drawings

PROCESS FOR REDUCING THE FREE ALDEHYDE CONTENT IN N-ALKYLOL AMIDE MONOMERS

BACKGROUND OF THE INVENTION

Latex binders are used in a wide variety of nonwoven and textile applications. In nonwovens, they are used to bind together a loosely assembled mass of fibers to form a self-sustaining web which can then be used to produce disposable diapers, consumer towels, disposable wipes, filtration products and the like. In textiles, they are used, for example, in fiberfill, upholstery backcoating, ticking coatings, flocking adhesives and high pile coatings. Depending upon the specific end use, the binders are formulated with other ingredients such as fillers, pigments, foaming agents, foam stabilizers, catalysts, thickeners and the like.

For many of these applications, it is desired to incorporate crosslinking monomers into the latex which, after application to the substrate, will crosslink in a weakly acidic pH range or in the presence of latent acid catalysts at elevated temperatures in order to improve the durability of the textile or nonwoven. Monomers derived from the reaction of a polymerizable amide with an aldehyde are conventionally utilized for such purposes. Generally, these N-alkylol amide containing monomers correspond to the structure:

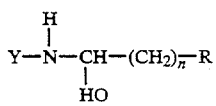

where Y is

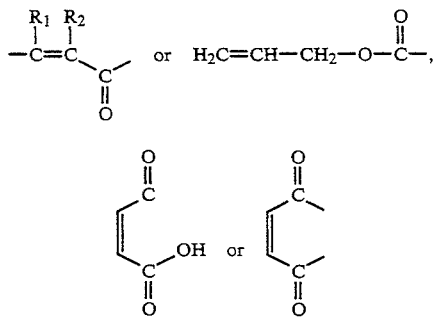

and where $R_1$ is H or $CH_3$; $R_2$ is H or $CH_3$; n is 0 to 3; R is H or $CH_3$ or

where $R_3$ is $C_1$ to $C_4$ alkyl or

and x is 2 to 4.

Of these monomers, N-methylol functional ethylenically unsaturated monomers are most often used. The N-(2,2-dialkoxy-1-hydroxy)ethyl acrylamide monomers are also examples of frequently used monomers of this type.

Although N-methylol acrylamide (NMA) is the most widely used crosslinking monomer in such applications, it is also a recognized source of formaldehyde, a chemical the presence of which manufacturers are seeking to eliminate or reduce. Thus, NMA is generally prepared by the reaction of a 1:1 molar mixture of aqueous acrylamide and formaldehyde under alkaline conditions (pH 9–10), a reaction leading to an equilibrium mixture containing NMA, acrylamide and formaldehyde in a ratio of approximately 96, 2.5 and 1.4%, respectively.

Previous attempts to shift the equilibrium towards lower free formaldehyde by increasing the pH of the reaction have led to undesirable side reactions such as polymerization of the acrylamide monomer or destruction of formaldehyde via the Cannizarro reaction. Another approach to lowering the free formaldehyde level is disclosed in U.S. Pat. No. 4,449,978 and involves using a molar excess of acrylamide in emulsion polymers prepared with NMA. Various scavengers have also been suggested, such as are taught in U.S. Pat. No. 5,143,954. However, the presence of these scavengers or their reaction products is not always desirable in the final product.

The amount of free formaldehyde present in emulsion binders which contain N-methylol acrylamide is quantifiable in three different aspects. The first is the free formaldehyde in the emulsion polymer as used. The second measurement is the free formaldehyde emitted by the emulsion polymer upon impregnation, coating, drying and curing in the nonwoven or textile product. The third measurement is free formaldehyde present in the finished nonwoven or textile material. The formaldehyde level in the final product is especially important in binders and coatings which are to be in direct contact with human skin such as in the case of baby diapers, paper towels and the like. The amount of formaldehyde emitted upon drying is also important in the conversion of large fabric rolls where the levels of formaldehyde which may be released into the work environment are limited.

When N-(2,2-dialkoxy-1-hydroxy)alkyl acrylamide monomers such as N-(2,2-dimethoxy-1-hydroxy)ethyl acrylamide (DMHEA) are used as the crosslinking monomer in latex binders, it is possible to produce binders which are entirely free of formaldehyde. However, since the reaction to produce the monomer also results in an equilibrium mixture, the presence of the free aldehyde component has been found to produce undesirable discoloration in the dried webs bonded therewith. It is therefore desirable to minimize the level of free dialkoxyacetaldehyde in the DMHEA monomer.

SUMMARY OF THE INVENTION

We have now found that the free aldehyde content of the emulsion polymer and in the finished nonwoven or textile may be substantially reduced by the use in the emulsion polymer of an N-alkylol amide monomer which has been treated under controlled pH and temperature conditions with an alkali or alkali earth metal borohydride to chemically convert the free aldehyde contained in the monomer to the corresponding alcohol.

Thus, the present invention is related to an improvement in the preparation of N-alkylol amide monomers wherein the improvement comprises adjusting the pH of the monomer to pH 10–11, and adding thereto an alkali or alkali earth metal borohydride at a temperature of about −10° to 25° C., preferably 0° to 10° C., so as to convert the residual free aldehyde in the equilibrium mixture to the corresponding alcohol. The reduction of the free aldehyde content according to the invention may be carried out by batch or continuous processes. The resultant monomer has a free aldehyde content less than about 0.4% and, when used as a crosslinking comonomer in vinyl ester and vinyl ester acrylic ester emulsions polymers and copolymers, provides a substantial reduction in free aldehyde in both the latex and in the final dried and finished product prepared therewith.

The process described in the present invention has been found to be useful in the reduction of formaldehyde in N-methylol functional ethylenically unsaturated monomers and also in the reduction of free aldehyde levels in N-(2,2-dialkoxy-1-hydroxy)alkyl acrylamide monomers as well as in similar N-alkylol amide monomers.

DETAILED DESCRIPTION OF THE PREFERRED EMBODIMENT

In accordance with the process of the invention, the N-alkylol amide containing monomer to be treated is prepared in aqueous solution by the reaction of a polymerizable amide with an aldehyde according to conventional techniques. For example, N-methylol acrylamide monomer is prepared by the reaction of equimolar amounts of formaldehyde and acrylamide at a pH of about 9.5–10 and a temperature ranging from 35° to 40° C. for about 3 hours until the formaldehyde level is less than about 2%, preferably between 1.2 and 1.5% as determined by hydroxylamine titration.

Analogous procedures are used for the preparation of other N-methylol functional ethylenically unsaturated carboxamides having 3–10 carbon atoms such as N-methylolmethacrylamide, N-methylolmaleimide, N-methylolmaleamic acid, N-methylol-maleamic acid esters, N-methylolallylcarbamate, N-methylolamides of the vinyl aromatic acids such as N-methylol-p-vinylbenzamide and the like.

Similarly, the N-(2,2-dialkoxy-1-hydroxy)ethyl acrylamide monomers are prepared by the reaction of acrylamide with the corresponding 2,2-dialkoxy acetaldehyde. Other N-alkylol amide can be similarly prepared via reaction of other polymerizable amides and other aldehydes.

After the reaction of the polymerizable amide with an aldehyde is complete (i.e., has essentially reached equilibrium), the borohydride reduction of residual free aldehyde is carried out. In this step, the alkali or alkali earth metal borohydride, preferably sodium borohydride, in a basic solution with sodium hydroxide or other base, is added to the monomer which has previously been adjusted to pH 10–11 and maintained at a temperature of about −10° to 25° C. Lower temperatures may be used provided care is taken to avoid crystallization of the N-alkylol amide. Addition of the borohydride is continued together with sufficient acid to maintain the desired pH and cooling to maintain the desired temperature for about one hour until titration of the residual aldehyde indicates levels of less than about 0.5%, after which the pH is adjusted to 6. The resultant scavenged monomer should be stored in a cool place at temperatures below about 30° C.

Theoretically one mole of borohydride is capable of reducing 4 moles of aldehyde; however, we have found that a borohydride to aldehyde molar ratio of 1:3 to 1:1 is preferred for optimum reduction of free aldehyde in the monomer. It is believed the need for the excess borohydride results from the generation of free aldehyde via re-equilibration of the adduct/amide/aldehyde system under the basic reaction conditions.

It should be noted that the borohydride reduction of the aldehyde is very rapid yet only moderately exothermic. However, the neutralization reaction with sulfuric acid is strongly exothermic. The exotherm can be easily controlled by controlling the addition rate of the reagents. Moreover, during the course of the reaction, the borohydride reduces the Cu(II) ions present in the acrylamide to elemental Cu. Cu(II) ions are present in acrylamide as free radical inhibitors; elemental Cu does not act as a free radical polymerization inhibitor. The addition of methoxy hydroquinone or other free radical inhibitors as well as good air sparge are therefore necessary to inhibit premature free radical polymerization of the monomer.

The resultant low aldehyde containing N-alkylol amide may be used alone as the crosslinking monomer in various emulsion polymer to lower the free aldehyde level in the emulsion polymer. The crosslinking monomer is generally used at levels of about 0.5 to 10%, preferably 1 to 5%, by weight of the polymer.

The primary monomers used in emulsion polymers prepared with the low aldehyde containing N-alkylol amide monomers include vinyl esters or copolymers of vinyl acetate with ethylene or acrylate esters. Generally emulsions prepared herein are derived from polymers which contain at least 50% by weight of the vinyl acetate or component which may be copolymerized with at least one of any conventionally employed comonomers. Suitable comonomers include those selected from the class of ethylene; vinyl chloride; vinyl esters of aliphatic carboxylic acids containing 1–20 carbon atoms; dialkyl esters of maleic and fumaric acid containing 1–8 carbon atoms in each alkyl group; and $C_1$–$C_8$ alkyl acrylates and methacrylates. These comonomers may be present in the emulsion copolymers at levels up to 48% by weight of the total polymer composition. In the case where ethylene is the comonomer, it is generally used in amounts up to about 30% by weight. Also suitable for polymerization with the low aldehyde N-alkylol amide monomers are emulsion polymers based entirely on $C_1$–$C_{14}$ alkyl (meth) acrylate esters as well as copolymers thereof.

As noted above, the crosslinking monomers used herein are the low aldehyde-containing N-alkylol amides which have been treated with a borohydride salt according to the teachings of the invention.

Olefinically-unsaturated carboxylic acids may be used in an emulsion polymer. These include the alkanoic acids having from 3 to 6 carbon atoms or the alkenedioic acids having from 4 to 6 carbon atoms, like acrylic acid, methacrylic acid, crotonic acid, itaconic acid, maleic acid or fumaric acid, or mixtures thereof in amounts sufficient to provide up to about 4% by weight, of monomer units in the final copolymer.

Optionally, polyunsaturated copolymerizable monomers may also be present in small amounts, i.e., up to about 1% by weight. Such comonomers would include those polyolefinically-unsaturated monomers copolymerizable with vinyl esters or vinyl ester acrylic ester copolymers for example, vinyl crotonate, allyl acrylate, allyl methacrylate, diallyl maleate, divinyl adipate, diallyl adipate, diallyl phthalate, ethylene glycol diacrylate, ethylene glycol dimethacrylate, butanediol dimethacrylate, methylene bis-acrylamide, triallyl cyanurate, etc. In addition, certain copolymerizable monomers which assist in the stability of the copolymer emulsion, e.g., sodium vinyl sulfonate, are also useful herein as latex stabilizer. These optionally present monomers, if employed, are added in very low amounts of from 0.1 to about 2% by weight of the monomer mixture.

The emulsions are prepared using conventional batch, semi-batch or semi-continuous emulsion polymerization procedures. Generally, the monomers are polymerized in an aqueous medium in the presence of the redox initiator system and at least one emulsifying agent.

If a batch process is used, the major monomer(s) and any optional non-functional monomers are dispersed in water and are thoroughly agitated while being gradually heated to the polymerization temperature. The homogenization period is followed by a polymerization period during which the initiator and functional monomers including the low aldehyde N-alkylol amide monomers are added incrementally or continuously. If the slow addition procedure is employed, and particularly in the case of polymerization of vinyl acetate with acrylate esters, the major monomer(s) and any optional comonomers are added gradually throughout the polymerization reaction. In either case, the polymerization is performed at conventional temperatures from about 40° C. to 110° C., preferably from 50° C. to 80° C., for sufficient time to achieve a low monomer content, e.g., from 0.5 to about 10 hours, preferably from 2 to about 6 hours, to produce a latex having less than 1 percent, preferably less than 0.2 weight percent, free monomer.

In the case of interpolymers containing ethylene, the polymerization procedure is similar to that discussed above except that it is carried out under pressure of 10 to about 130 atmospheres using polymerization procedures taught, for example, in U.S. Pat. Nos. 3,708,388; 3,404,112; 3,380,851 and 4,164,488. In these cases, the ethylene content of the interpolymer depends on the ethylene content of the aqueous polymerization medium. Factors which control the ethylene content of the polymerization medium include the partial pressure of ethylene in the vapor phase over the medium, the temperature of polymerization and the degree of mixing between the vapor phase and the liquid medium. Generally, the polymerization is performed at temperatures from 50° C. to 80° C. and, at these temperatures, ethylene partial pressures from 50 to 1,500, preferably from 250 to 1,000 psig, are sufficient to incorporate from 1 to 30, preferably from 5 to 25, weight percent ethylene in the polymer.

While any conventional initiator systems may be utilized herein, the use of a particular polymerization initiator system comprising a hydrophobic hydroperoxide, in amounts of between 0.05 and 3% by weight, preferably 0.1 and 1% by weight based on the total amount of the emulsion and ascorbic acid, in amounts of 0.05 to 3% by weight, preferably 0.1 to 1% by weight, based on the total amount of the emulsion has been found to provide an additional reduction in the free formaldehyde content of the resultant polymer. As used herein, the term "ascorbic acid" includes additionally the isomers of ascorbic acid such as iso-ascorbic acid (i.e., erythoric acid). Hydrophobic hydroperoxides include, for example, tertiary butyl hydroperoxide, tertiary amyl hydroperoxide, cumene hydroperoxide and the like. Of the hydrophobic hydroperoxides, tertiary butyl is preferred. The redox initiator system is slow-added during the polymerization.

To control the generation of free radicals, a transition metal is often incorporated into the redox system, and such metals include an iron salt, e.g., ferrous and ferric chloride and ferrous ammonium sulfate. The use of transition metals and levels of addition to form a redox system for polymerization media are well-known.

The polymerization is carried out at a pH of between 2 and 7, preferably between 3 and 5. In order to maintain the pH range, it may be useful to work in the presence of customary buffer systems, for example, in the presence of alkali metal acetates, alkali metal carbonates, alkali metal phosphates. Polymerization regulators such as mercaptans, chloroform, methylene chloride and trichloroethylene, can also be added in some cases.

The dispersing agents are all the emulsifiers generally used in emulsion polymerization, as well as optionally present protective colloids. It is also possible to use emulsifiers alone or in mixtures with protective colloids.

The emulsifiers can be anionic, cationic or nonionic surface active compounds. Suitable anionic emulsifiers are, for example, alkyl sulfonates, alkylaryl sulfonates, alkyl sulfates, sulfates of hydroxylalkanols, alkyl and alkylaryl disulfonates, sulfonated fatty acids, sulfates and phosphates of polyethoxylated alkanols and alkyphenols, as well as esters of sulfosuccinic acid. Suitable cationic emulsifiers are, for example, alkyl quaternary ammonium salts, and alkyl quaternary phosphonium salts. Examples of suitable non-ionic emulsifiers are the addition products of 5 to 50 moles of ethylene oxide adducted to straight-chained and branch-chained alkanols with 6 to 22 carbon atoms, or alkylphenols, of higher fatty acids, or higher fatty acid amides, or primary and secondary higher alkyl amines; as well as block copolymers of propylene oxide with ethylene oxide and mixtures thereof. When combinations of emulsifying agents are used, it is advantageous to use a relatively hydrophobic emulsifying agent in combination with a relatively hydrophilic agent. The amount of emulsifying agent is generally from about 1 to 10, preferably from about 2 to about 8, weight percent of the monomers used in the polymerization.

The emulsifier used in the polymerization can also be added in its entirety to the initial charge to the polymerization zone or a portion of the emulsifier, e.g., from 25 to 90 percent thereof, can be added continuously or intermittently during polymerization.

Various protective colloids may also be used in addition to the emulsifiers described above. Suitable colloids include polyvinyl alcohol, partially acetylated polyvinyl alcohol, e.g., up to 50 percent acetylated, casein, hydroxyethyl starch, carboxymethyl cellulose, gum arabic, and the like, as known in the art of synthetic emulsion polymer technology. In general, these colloids are used at levels of 0.05 to 4% by weight, based on the total emulsion.

The polymerization reaction is generally continued until the residual vinyl acetate monomer content is below about 1%, preferably less than 0.2%. The completed reaction product is then allowed to cool to about room temperature, while sealed from the atmosphere.

The emulsions are produced and used at relatively high solids contents, e.g., between 35 to 70%, preferably not less than 50%, although they may be diluted with water if desired.

Optionally, the resultant latex may be post-scavenged to further reduce the level of free aldehyde present. The post scavengers are known in the art and include ethylene urea, acetoacetamide, as well as the scavengers taught in U.S. Pat. No. 5,143,954, the disclosure of which is incorporated herein by reference.

Furthermore, since the latex contain such low levels of aldehyde, it may be necessary or desirable to add thereto non-formaldehyde containing preservatives or bacteriocides such as Kathon available from Rohm and Haas.

The particle size of the latex can be regulated by the quantity of nonionic or anionic emulsifying agent or protective colloid employed. To obtain smaller particles sizes, greater amounts of emulsifying agents are used. As a general rule, the greater amount of the emulsifying agent employed, the smaller the average particle size.

The following examples are given to illustrate the present invention, but it will be understood that they are intended to be illustrative only and not limitative of the invention. In the examples, all parts are by weight unless otherwise indicated. In the examples, the following procedure was used to determine the sodium borohydride level.

Assay of Sodium Borohydride by the Periodate Method

1. Accurately weigh 0.5 g sample of dry sodium borohydride into a 250 mL volumetric flask. Dissolve it in 1.0N sodium hydroxide. Dilute to the mark with 1.0N sodium hydroxide and mix well.
2. Pipet 10 mL aliquot into a clean iodine flask and immediately add 35.0 mL of 0.04M potassium periodate solution.
3. Add 2.0 g potassium iodide. Swirl gently to dissolve KI crystals.
4. Add 10 mL of 6N sulfuric acid, stopper, swirl to mix and allow to stand in a cool, dark place for 2-3 minutes.
5. Wash down the stopper and the sides of the flask with distilled water. Titrate with 0.1N sodium thiosulfate solution, using starch indicator, to a colorless endpoint.
6. Calculate % sodium borohydride as follows:

$$\% \text{ NaBH}_4 = \frac{[(\text{mL KIO}_3) \times \text{N KIO}_3) - (\text{mL Na}_2\text{S}_2\text{O}_3 \times \text{N Na}_2\text{S}_2\text{O}_3)] \times 0.4731}{\text{Sample weight (grams)}}$$

EXAMPLE I

This example describes the preparation of low formaldehyde N-methylol acrylamide in accordance with the teachings of the invention.

The following charges were prepared:

| | | Wt (g) | mole |
|---|---|---|---|
| | Initial Charge | | |
| 1. | Acrylamide 50 wt % | 210 | 1.48 |
| 2. | Formaldehyde, 50 wt % | 44.6 | 0.74 |
| | Subsequently Added | | |
| 3. | NaOH 25 wt % | 0.50 | 0.013 |
| 4. | Formaldehyde, 50 wt % | 44.6 | 0.74 |
| 5. | Methyl ether of hydroquinone (MEHQ) | 0.007 | 50 ppm |
| | Reductant Slow Add | | |
| 6. | NAOH 25 wt % | 1.6 | 0.04 |
| 7. | DI Water | 8.4 | |

-continued

| | | Wt (g) | mole |
|---|---|---|---|
| 8. | NaBH$_4$ | 1.8 | 0.047 |
| | Acid Slow Add | | |
| 9. | DI Water | 3.1 | |
| 10. | H$_2$SO$_4$ 98 wt % | 3.1 | 0.031 |
| 11. | MEHQ | 0.007 | 50 ppm |
| | Total | 318.5 | |

Apparatus

1-L Reaction flask equipped with a 2" anchor-type SS stirrer, thermometer, pH probe, sub-surface air inlet, hot water bath (for NMA preparation), 2 addition funnels, and ice-salt cooling bath (for borohydride reduction). The additional funnels for borohydride and the acid must be set as far apart as possible to avoid any contact of unreacted borohydride with the acid going into the reaction.

Procedure

The preparation of low formaldehyde NMA is carried out in two stages. First, the NMA is prepared from 1:1 molar mixture of acrylamide and formaldehyde at high pH. In the second stage (step 7 onwards), the free formaldehyde is reduced with borohydride at low temperature ($-10°$ to 25° C.) and high pH (10-11) as described previously. The reducing agent and the sulfuric acid solutions should be kept ready in time for the second stage to start immediately following the first stage as NMA is not very stable at high pH even at room temperature.

1. Assay acrylamide and formaldehyde for concentration using standard analytical methods.
2. Place acrylamide "1" and formaldehyde "2" in the flask. Start stirrer and air sparge.
3. Add sodium hydroxide "3" to adjust pH between 9.5-10. The reaction with exotherm to 30°-35° C. This exotherm is dependent on the reaction scale and a water bath may be used to cool the reaction. Do not allow the reaction to exotherm beyond 45° C.
4. After the exotherm has subsided, add the second half of the formaldehyde "4" and adjust pH if necessary with NaOH "3". The pH must not exceed 10 and the temperature must not exceed 45° C. Warm the reaction mixture to 35°-40° C. and continue the reaction until the formaldehyde level is <2% preferably between 1.2 to 1.5% as determined by conventional hydroxylamine titration. This takes approximately 3 hours.
5. Add MEHQ "5" to the reaction mixture and stir until dissolved. Adjust the reaction mixture to pH 10-11 with NaOH "3" as necessary.
6. Cool the reaction mixture to 25° C. and proceed to carry out the reduction of the free formaldehyde with borohydride which is described starting from step 7.
7. In a 50 mL conical flask equipped with a 1" magnetic stirrer, make a solution of NaOH "6" in water "7" and cool to 25° C.
8. Add the sodium borohydride in small portions to the NaOH solution in step 7 with good stirring over 10 minutes. Stir well until all the borohydride is dissolved.
9. Titrate the borohydride for activity using the periodate method. Adjust the quantity of the solution to the required amount in the formula. The activity of sodium borohydride should be 15±0.2%. Transfer this solution to one of the addition funnel.
10. Place water "9" in a 50 mL beaker and slowly add sulfuric acid "10" with good mixing so as not to cause excessive heat build up. A suitable cooling bath may be used to control the exotherm. Let the solution cool to 25° C. before placing it in the addition funnel.
11. Cool the reaction mixture prepared in step 6 to 8°-10° C. The reduction temperature must be maintained below 10° C. to achieve the desired low final formaldehyde level.
12. Start borohydride slow add "B" followed by sulfuric acid slow add "C" at such a rate to maintain pH between 10-11 and temperature below 10° C. At 500 mL scale in the laboratory, the addition times are about 1 hour. During this step MEHQ and good air sparge are necessary to inhibit premature free radical polymerization of the monomer.
13. After the borohydride slow add is complete, immediately bring the pH to 5-6 with sulfuric acid solution prepared in step 10. Let the reaction mixture warm to room temperature. As both the reduction and the neutralization are diffusion controlled reactions, very good agitation is necessary to avoid any build up of local concentration of the reagents. The localized concentration of reagents may result in unwanted gelation of the product (probably via anionic polymerization).
14. Add the MEHQ "11" and stir until dissolved. Remove an aliquot and perform residual formaldehyde titration and water content (for solids). Transfer to a suitable container and store in a cool place below about 30° C. The resulting monomer was characterized as follows.

| Property | Value |
| --- | --- |
| Solids wt % | 46-49 |
| Calculated NMA* | 42-45 |
| Free formaldehyde, wt %** | 0.10-0.15 |

*The active NMA % is calculated from the % active NMA in the initial charge as follows:

$$\text{\% Active NMA in the final product} = \frac{\text{\% active NMA in the initial charge}}{\text{Total weight of final solution}}$$

**Free formaldehyde was determined using the method described by S. Siggia and J. G. Hanna in Quantitative Organic Analysis via Functional Groups, J. Wiley & Sons, p. 95.

Maintaining the pH between 10-11 is critical to obtaining gel free monomer and lower temperature is critical in being able to achieve the desired low formaldehyde level. This requirement is illustrated by the results presented in the following table wherein the interaction of temperature and pH level are described.

TABLE I

| Temperature, °C. ↓ | Residual free CH₂O (%) as a function of temperature and pH | | | |
| --- | --- | --- | --- | --- |
| | | | | |
| 25 | GEL | | | 0.54 |
| 17.5 | | 0.23 | 0.27 | |
| 10 | GEL | 0.14 | 0.11 | 0.12 |
| pH → | 9 | 10 | 10.5 | 11 |

The results presented in Table I illustrate the interrelationship between the temperature of the reaction and the pH at which it is carried out. Thus, at pH of about 9, gelation occurs. Moreover, at temperatures about 25° C. and at pH of about 12, the level of formaldehyde present in the monomer increases above about 0.5 ppm.

Thus, the results of Table I show that optimum conditions are obtained at pH of 10-11 and temperatures of 5° to 20° C, preferably 5° to 20° C.

Another series of N-methylol acrylamide products were prepared to illustrate the effects of the formaldehyde/borohydride ratio as well as even lower temperatures (−10.5° to +5° C.) on the free formaldehyde level. The samples were prepared at pH 10.5 and tested as described previously. The results are shown below.

TABLE II

| Formaldehyde: Borohydride Mole Ratio | Formaldehyde (as pph of NMA) | Reaction Temperature (°C.) |
| --- | --- | --- |
| 3:1 | 0.32 | 3 to 5 |
| 2.5:1 | 0.1 | 3 to 5 |
| 2:1 | 0.04 | 3 to 5 |
| 1:1 | 0.004 | 3 to 5 |
| 3:1 | 0.07 | −10.5 to −8.5 |
| 4:1 | 0.4 | −10.5 to −8.5 |

As illustrated in Table II, at a fixed temperature as the amount of borohydride increases, the level of formaldehyde decreases. Additionally, lowering the temperature at which the scavenging reaction is performed, substantially decreases the level of formaldehyde in the resultant product.

EXAMPLE II

An aqueous solution of N-(2,2-dimethoxy-1-hydroxy)ethyl acrylamide (DMHEA) prepared by the condensation of an equimolar mixture of 50% acrylamide and 50% 2,2-dimethoxy acetaldehyde (DMA) at pH 9-10 resulted in a monomer mixture containing 39% DMHEA, 5% DMA and 3% acrylamide. This solution when subjected to the sodium borohydride reduction under conditions similar to that described for N-methylol acrylamide in Example I resulting in a monomer mixture containing approximately 39% DMHEA, 0.25% DMA, 4.8% 2,2-dimethoxy ethanol (reduction of DMA) and 3% acrylamide.

EXAMPLE III

The following example illustrates the batch preparation of the emulsion polymers containing the low formaldehyde N-methylol acrylamide prepared in Example I at pH 10.5 and 10° C.

A 10 liter stainless steel autoclave equipped with heating/cooling means, variable rate stirrer and means of metering monomers and initiators was employed. To the 10 liter autoclave was charged 400 g (of a 20% w/w solution) sodium alkyl aryl polyethylene oxide sulphate (3 moles ethylene oxide), 60 g (of a 70% w/w solution in water) alkyl aryl polyethylene oxide (30 mole ethylene oxide), 70 g sodium vinyl sulfonate (25% solution in water), 0.5 g sodium acetate, 5 g (of a 1% solution in water) ferrous sulfate solution, 1.7 g ascorbic acid and 2000 g water. After purging with nitrogen, all the vinyl acetate (3600 g) was added and the reactor was pressurized to 600 psi with ethylene and equilibrated at 50° C. for 15 minutes.

After heating to 50° C., the polymerization was started by metering in a solution of 16 g tertiary butyl hydroperoxide (tBHP) in 250 g of water and 10 g ascorbic acid in 250 g water. The initiators were added at a uniform rate over a period of 5¼ hours.

Concurrently added with the initiators over a period of 4 hours was an aqueous solution of 395 g of the N-methylol acrylamide from Example 1 (44% w/w solution in water), 1.5 g of sodium acetate in 400 g of water and 150 g (of a 20% w/w solution) sodium alkyl aryl polyethylene oxide sulfate (3 moles ethylene oxide).

During the reaction the temperature was controlled at 75° C. to 80° C. by means of jacket cooling. At the end of the reaction the emulsion was transferred to an evacuated vessel (30 L) to remove residual ethylene from the system. An additional 1.6 g of tBHP in 25 g water and 1 g ascorbic acid in 25 g water were added to reduce the residual monomer to less than 0.5%.

This procedure resulted in a polymeric composition of ethylene, vinyl acetate and N-methylol acrylamide (E/VA/NMA) in a 18:82:4 ratio.

For comparative purposes, Control I was prepared with N-methylol acrylamide which had not been treated with the borohydride. The polymer was prepared as above using ascorbic acid and t-butyl hydroperoxide as the polymerization catalyst system. Control II was also prepared with untreated N-methylol acrylamide but using sodium formaldehyde sulfoxydration as the polymerization catalyst. Control III was prepared using NMA Special, a 48% w/w solution containing 28% NMA and 20% acrylamide available from American Cyanamid.

Test Procedure

In preparing the samples for testing, sections of a cellulosic pulp substrate were saturated using a Werner Mathis-type VFM Padder and a bath of 100 parts dry binder, 1 part catalyst and sufficient water to dilute to a 10% solids concentration, to a dry pick up of approximately 8 to 15 parts binder per 100 parts pulp web. The saturated web was dried for 1 minute at 100° C. in a laboratory contact drier and cured an additional 2 minutes at 149° C. in a forced air oven. The samples were conditioned overnight in a controlled temperature and humidity room.

The tensile tests were run on a standard Instron tensile tester set at 3 inch gauge length and 1 inch/minute crosshead speed. The wet tensile strength was tested after soaking specimens for one minute in a 1.0% solution of Aerosol OT wetting agent. Results shown reflect the average of 10 tests.

In these examples, web formaldehyde is determined on Whatman filter paper using an acetylacetone test procedure which utilizes the Nash reagent. The Nash reagent is a solution containing 0.2M acetylacetone, 0.05M acetic acid, and 2M ammonium acetate and has a pH of 6.6. Under the conditions of the assay method formaldehyde reacts with the reagent to produce a lutidine compound in a highly specific reaction.

The formaldehyde is extracted with deionized water. The colorimetric analysis is based on the reaction of formaldehyde with acetylacetone. The absorbency of the yellow-colored by-product is measured on a visible spectrophotometer at 412 nm and the concentration of free formaldehyde is determined with reference to a standard calibration curve.

The quantitative analysis of free formaldehyde in the latex involves a high performance liquid chromatography (HPLC) procedure which selectively determines the Nash reagent-formaldehyde derivative. Values are reported in parts per million (ppm) on the latex as made.

TABLE III

| SAMPLE | X-LINK MONOMER | AMOUNT | HCHO IN LATEX | IN WEB | CMD TENSILE PERFORMANCE | | |
|---|---|---|---|---|---|---|---|
| | | | | | DRY | WET | M.E.K. |
| 1 | Monomer of Sample 1 | 4.0 | 45 | 6 | 10.86 | 4.76 | 3.76 |
| Control I | Unscavenged NMA Control-Ascorbic Acid | 4.0 | 460 | 18 | 8.60 | 3.60 | 2.51 |
| Control II | Unscavenged NMA Control - SFS | 5.2 | 670 | 74 | 9.35 | 4.42 | 3.28 |
| Control III | Control (NMA Special) | 5.2 | 61 | 6 | 9.82 | 3.90 | 2.83 |

As the results presented in Table III show, the level of formaldehyde in the dried web (less than 10 ppm) is substantially reduced in the samples prepared with the low formaldehyde NMA monomer when compared with other emulsions containing comparable untreated NMA monomer. Moreover, the samples prepared in accordance with the teachings of the present invention also exhibit substantial performance improvements as shown by the wet and dry tensile strength properties wherein only 4 parts of the borohydride treated NMA were required to give properties comparable results to those obtained with 5.2 parts of the untreated NMA or of the NMA Special.

Similar results would be obtained using the low formaldehyde N-methylol amide monomers in other vinyl ester or acrylic polymers.

We claim:

1. In the process for the preparation of polymerizable olefinically unsaturated N-alkylol amide monomers wherein a polymerizable amide is reacted with an aldehyde, the improvement which comprises adjusting the pH of the resulting polymerizable olefinically unsaturated N-alkylol amide cross-linking monomer to pH 10–11 and adding thereto an alkali or alkali earth metal borohydride at a temperature of −10° to 20° C. so as to convert the residual free aldehyde in the equilibrium mixture to the corresponding alcohol thereby providing a residual aldehyde content of less than 0.4%.

2. The process of claim 1 wherein the N-alkylol amide monomer is N-methylol acrylamide.

3. The process of claim 1 wherein the N-alkylol amide monomer is an N-(2,2-dialkoxy-1-hydroxy)alkyl acrylamide.

4. The process of claim 1 wherein the borohydride is added in an amount to provide a borohydride to aldehyde molar ratio between 1:3 and 1:1.

5. A polymerizable olefinically unsaturated N-alkylol amide monomer produced by the process of claim 1 and containing less than 0.4% free aldehyde.

6. In a process for the production of a low formaldehyde emulsion polymer containing at least 50% by weight vinyl acetate and up to 10% by weight of a polymerizable olefinically unsaturated N-alkylol amide crosslinking monomer wherein the polymerization is carded out in water in the presence of a redox initiator system, the improvement which comprises using as the crosslinking monomer a polymerizable olefinically unsaturated N-alkylol amide which has been treated by adjusting the pH to 10–11 and adding thereto an alkali or alkali earth metal borohydride at a temperature of −10° to 20° C. so as to convert the residual free aldehyde in the equilibrium mixture to the corresponding alcohol thereby providing a residual formaldehyde content of less than 0.4%.

7. The process of claim 6 wherein the redox initiator system comprises 0.05 to 3% by weight of the polymer solids of a hydrophobic hydroperoxide and 0.05 to 3% by weight ascorbic acid.

8. The process of claim 7 wherein the hydrophobic hydroperoxide is tertiary butyl hydroperoxide.

9. The process of claim 7 wherein the hydrophobic hydroperoxide is present in an amount of 0.1 to 1% and the ascorbic acid is present in an amount of 0.1 to 1%.

10. The process of claim 6 wherein the vinyl acetate is polymerized with up to 30% by weight ethylene.

11. The process of claim 6 wherein the crosslinking monomer is N-methylol acrylamide.

12. The process of claim 6 wherein the crosslinking monomer is an N-(2,2-dialkoxy-1-hydroxy)alkyl acrylamide.

13. A nonwoven product comprising a nonwoven web of fibers bonded together with a binder which comprises an emulsion polymer produced by the process of claim 6, the nonwoven product characterized by a low free formaldehyde content after drying and curing at a binder add-on which is sufficient to bind the fibers together to form a self-sustaining web.

14. A nonwoven product comprising a nonwoven web of fibers bonded together with a binder which comprises an emulsion polymer produced by the process of claim 7, the nonwoven product characterized by a low free formaldehyde content after drying and curing at a binder add-on which is sufficient to bind the fibers together to form a self-sustaining web.

15. A textile product comprising a textile substrate coated with an emulsion polymer prepared by the process of claim 6, the textile product characterized by a low free formaldehyde content after drying and curing.

16. A textile product comprising a textile substrate coated with an emulsion polymer prepared by the process of claim 7, the textile product characterized by a low free formaldehyde content after drying and curing.

17. A low formaldehyde containing emulsion polymer comprising at least 50% by weight vinyl acetate and up to 10% by weight of a crosslinking monomer, the crosslinking monomer having been treated by adjusting the pH to 10–11 and adding thereto an alkali or alkali earth metal borohydride at a temperature of −10° to 20° C. so as to convert the residual free aldehyde in the equilibrium mixture to the corresponding alcohol and the emulsion binder having been polymerized using an initiator system which consists of 0.01 to 3% by weight tertiary butyl hydroperoxide and 0.01 to 3% by weight ascorbic acid.

* * * * *